US009883975B2

(12) United States Patent
Glaug et al.

(10) Patent No.: US 9,883,975 B2
(45) Date of Patent: Feb. 6, 2018

(54) TAMPON PLEDGET WITH IMPROVED BY-PASS LEAKAGE PROTECTION

(71) Applicant: Edgewell Personal Care Brands, LLC, Chestefield, MO (US)

(72) Inventors: Frank S. Glaug, Chester Springs, PA (US); Keith J. Edgett, Middletown, DE (US); Eugene P. Dougherty, Camden-Wy, DE (US)

(73) Assignee: Edgewell Personal Care Brands, LLC, Chesterfield, MO (US)

( * ) Notice: Subject to any disclaimer, the term of this patent is extended or adjusted under 35 U.S.C. 154(b) by 698 days.

(21) Appl. No.: 14/168,440

(22) Filed: Jan. 30, 2014

(65) Prior Publication Data

US 2014/0215779 A1  Aug. 7, 2014

Related U.S. Application Data

(62) Division of application No. 12/115,845, filed on May 6, 2008, now abandoned.

(51) Int. Cl.
*B32B 37/00* (2006.01)
*A61F 13/20* (2006.01)
(Continued)

(52) U.S. Cl.
CPC ........ *A61F 13/204* (2013.01); *A61F 13/2051* (2013.01); *A61F 13/2065* (2013.01);
(Continued)

(58) Field of Classification Search
CPC .............. A61F 13/2097; A61F 13/2015; A61F 13/2065; A61F 13/2085; B29C 65/08
(Continued)

(56) References Cited

U.S. PATENT DOCUMENTS 1,401,358 A   12/1921  Peterkin
2,330,257 A    9/1943  Bailey
(Continued)

FOREIGN PATENT DOCUMENTS

BE         768046 A    11/1971
CA       2127144 A1    10/1995
(Continued)

OTHER PUBLICATIONS

Examination Report for corresponding GB Application No. GB1117582.5, Date of Report Mar. 27, 2013, pp. 1-2.
(Continued)

*Primary Examiner* — James Sells
(74) *Attorney, Agent, or Firm* — Edgewell Personal Care Brands, LLC (57) ABSTRACT

A tampon has two pledgets or one pledget with an absorbent layer and a leak shield located therebetween. The pledgets or pledget with the absorbent layer and the leak shield are folded such that the leak shield covers a portion of the surface of at least one of the pledgets. Both pledgets or the one pledget with the absorbent layer have absorbencies that are each greater than an absorbency of the leak shield. In another embodiment of the tampon, the leak shield comprises a fluid impervious or fluid repellent material(s). In another embodiment of the tampon, the leak shield comprises of an absorbent or hydrophilic material. Yet in another embodiment, the leak shield comprises of multiple layers of materials that are hydrophilic, hydrophobic, or a combination thereof. A method of fabricating a tampon includes forming a pledget, combining a fluid-impervious polymer material with an absorbent material to define a polymer laminate, ramming the pledget and the laminate into an oven tube, and stitching the laminate to the pledget.

24 Claims, 11 Drawing Sheets

(51) Int. Cl.
  *B29C 65/08* (2006.01)
  *A61F 13/26* (2006.01)
  *A61F 13/34* (2006.01)
  *B29K 23/00* (2006.01)
  *B29K 67/00* (2006.01)

(52) U.S. Cl.
  CPC ...... *A61F 13/2074* (2013.01); *A61F 13/2085* (2013.01); *A61F 13/2097* (2013.01); *A61F 13/26* (2013.01); *A61F 13/34* (2013.01); *B29C 65/08* (2013.01); *B29K 2023/12* (2013.01); *B29K 2067/003* (2013.01)

(58) Field of Classification Search
  USPC ....................................................... 156/73.1
  See application file for complete search history.

(56) References Cited

U.S. PATENT DOCUMENTS

| | | |
|---|---|---|
| 2,391,343 A | 12/1945 | Popper |
| 2,412,861 A | 12/1946 | George et al. |
| 2,499,414 A | 3/1950 | Rebell |
| 2,761,449 A | 9/1956 | Bletzinger |
| 3,051,177 A | 8/1962 | Wilson |
| 3,079,921 A | 3/1963 | Brecht et al. |
| 3,340,874 A | 9/1967 | Burgeni |
| 3,371,666 A | 3/1968 | Leaving |
| 3,397,695 A | 8/1968 | Voss |
| 3,465,390 A | 9/1969 | Mooney |
| 3,572,341 A | 3/1971 | Glassman |
| 3,606,643 A | 9/1971 | Mooney |
| 3,610,243 A | 10/1971 | Jones, Sr. |
| 3,618,605 A | 11/1971 | Glassman |
| 3,628,534 A | 12/1971 | Donohue |
| 3,643,661 A | 2/1972 | Crockford |
| 3,683,912 A | 8/1972 | Olsen et al. |
| 3,695,270 A | 10/1972 | Dostal |
| 3,699,965 A | 10/1972 | Dostal |
| 3,712,305 A | 1/1973 | Wennerblom et al. |
| 3,731,687 A | 5/1973 | Glassman |
| RE27,677 E | 6/1973 | Glassman |
| 3,738,364 A | 6/1973 | Brien et al. |
| 3,749,094 A | 7/1973 | Duncan |
| 3,811,445 A | 5/1974 | Dostal |
| 3,834,389 A | 9/1974 | Dulle |
| 3,981,305 A | 9/1976 | Ring |
| 4,200,101 A | 4/1980 | Glassman |
| 4,212,301 A | 7/1980 | Johnson |
| 4,274,412 A | 6/1981 | Austin |
| 4,318,407 A | 3/1982 | Woon |
| 4,335,720 A | 6/1982 | Glassman |
| 4,335,721 A | 6/1982 | Matthews |
| 4,373,529 A | 2/1983 | Lilaonitkul et al. |
| 4,374,522 A | 2/1983 | Olevsky |
| 4,543,098 A | 9/1985 | Wolfe et al. |
| 4,627,849 A | 12/1986 | Walton et al. |
| 4,787,895 A | 11/1988 | Stokes et al. |
| 4,836,587 A | 6/1989 | Hinzmann |
| 4,973,302 A | 11/1990 | Armour et al. |
| 5,004,467 A | 4/1991 | Hinzmann et al. |
| 5,006,116 A | 4/1991 | Alikhan et al. |
| 5,047,024 A | 9/1991 | Glassman |
| 5,112,348 A | 5/1992 | Glassman |
| 5,149,332 A | 9/1992 | Walton et al. |
| 5,153,971 A | 10/1992 | Van Iten |
| 5,314,743 A | 5/1994 | Meirowitz et al. |
| 5,364,383 A | 11/1994 | Hayes et al. |
| 5,389,067 A | 2/1995 | Rejai |
| 5,443,776 A | 8/1995 | Bartholomew et al. |
| 5,471,820 A | 12/1995 | Oppe et al. |
| 5,634,248 A | 6/1997 | Mcnelis et al. |
| 5,659,934 A | 8/1997 | Jessup et al. |
| 5,681,894 A | 10/1997 | Williams et al. |
| 5,755,906 A | 5/1998 | Achter et al. |
| 5,788,910 A | 8/1998 | Mcnelis et al. |
| 5,795,346 A | 8/1998 | Achter et al. |
| 5,804,653 A | 9/1998 | Weng |
| 5,807,372 A | 9/1998 | Balzar |
| 5,827,256 A | 10/1998 | Balzar |
| 5,873,971 A | 2/1999 | Balzar |
| 5,891,081 A | 4/1999 | Mcnelis et al. |
| 5,891,123 A | 4/1999 | Balzar |
| 5,931,803 A | 8/1999 | Jackson |
| 5,986,000 A | 11/1999 | Williams et al. |
| 6,039,716 A | 3/2000 | Jessup et al. |
| 6,039,828 A | 3/2000 | Achter et al. |
| 6,045,526 A | 4/2000 | Jackson |
| 6,142,984 A | 11/2000 | Brown et al. |
| 6,177,608 B1 | 1/2001 | Weinstrauch |
| 6,179,802 B1 | 1/2001 | Jackson |
| 6,183,436 B1 | 2/2001 | Korteweg et al. |
| 6,186,994 B1 | 2/2001 | Bowles et al. |
| 6,186,995 B1 | 2/2001 | Tharpe, Jr. |
| 6,248,274 B1 | 6/2001 | Williams |
| 6,333,108 B1 | 12/2001 | Wilkes et al. |
| 6,353,146 B1 | 3/2002 | Williams |
| 6,419,777 B1 | 7/2002 | Achter et al. |
| 6,478,726 B1 | 11/2002 | Zunker |
| 6,506,958 B2 | 1/2003 | Williams |
| 6,511,452 B1 | 1/2003 | Rejai et al. |
| 6,558,370 B2 | 5/2003 | Moser |
| 6,585,300 B1 | 7/2003 | Rajala et al. |
| 6,595,974 B1 | 7/2003 | Pauley et al. |
| 6,596,919 B2 | 7/2003 | Williams |
| 6,603,054 B2 | 8/2003 | Chen et al. |
| 6,635,205 B2 | 10/2003 | Williams et al. |
| 6,635,800 B2 | 10/2003 | Jackson et al. |
| 6,682,513 B2 | 1/2004 | Agyapong et al. |
| 6,702,797 B2 | 3/2004 | Williams |
| 6,719,743 B1 | 4/2004 | Wada |
| 6,740,070 B2 | 5/2004 | Agyapong et al. |
| D492,033 S | 6/2004 | Jarmon et al. |
| 6,746,418 B1 | 6/2004 | Pauley et al. |
| 6,814,722 B2 | 11/2004 | Jackson et al. |
| 6,830,554 B2 | 12/2004 | Jackson et al. |
| 6,886,443 B2 | 5/2005 | Rejai |
| 6,887,226 B2 | 5/2005 | Cassoni et al. |
| 6,890,324 B1 | 5/2005 | Jackson et al. |
| 6,923,789 B2 | 8/2005 | LeMay et al. |
| 6,932,805 B2 | 8/2005 | Domeier et al. |
| 6,953,456 B2 | 10/2005 | Fuchs et al. |
| 7,044,928 B2 | 5/2006 | LeMay et al. |
| 7,160,279 B2 | 1/2007 | Pauley et al. |
| 7,226,436 B2 | 6/2007 | Gorham et al. |
| 7,250,129 B2 | 7/2007 | Williams et al. |
| 7,335,194 B2 | 2/2008 | Wada |
| 7,387,622 B1 | 6/2008 | Pauley et al. |
| D572,362 S | 7/2008 | Edgett et al. |
| D579,113 S | 10/2008 | Edgett et al. |
| 7,563,401 B2 | 7/2009 | Pham et al. |
| D612,940 S | 3/2010 | Edgett et al. |
| 7,678,095 B2 | 3/2010 | Jackson et al. |
| 7,704,242 B2 | 4/2010 | LeMay et al. |
| 7,727,208 B2 | 6/2010 | LeMay et al. |
| 7,727,210 B2 | 6/2010 | LeMay et al. |
| 7,740,787 B2 * | 6/2010 | Hubbard, Jr. ....... A61F 13/2085 264/313 |
| 7,745,686 B2 | 6/2010 | Mauro et al. |
| 7,780,892 B2 | 8/2010 | Miller et al. |
| 7,798,986 B2 | 9/2010 | Melvin et al. |
| 7,799,966 B2 | 9/2010 | Williams et al. |
| 7,815,594 B2 | 10/2010 | Dougherty, Jr. et al. |
| D626,650 S | 11/2010 | Edgett et al. |
| 7,862,533 B2 | 1/2011 | LeMay et al. |
| 7,867,209 B2 | 1/2011 | Jorgensen et al. |
| 7,887,525 B2 | 2/2011 | Gorham et al. |
| 7,981,347 B2 * | 7/2011 | Hubbard, Jr. ....... A61F 13/2085 264/313 |
| 8,070,710 B2 | 12/2011 | Dougherty, Jr. |
| 8,093,446 B2 | 1/2012 | Knuth et al. |
| 8,166,834 B2 | 5/2012 | Dougherty, Jr. et al. |
| 8,197,434 B2 | 6/2012 | LeMay et al. |
| 8,198,504 B2 | 6/2012 | Glaug et al. |

(56) References Cited

U.S. PATENT DOCUMENTS

| | | |
|---|---|---|
| 8,221,375 B2 | 7/2012 | LeMay et al. |
| 8,323,256 B2 | 12/2012 | Edgett et al. |
| 8,372,027 B2 | 2/2013 | LeMay et al. |
| 8,444,590 B2 | 5/2013 | LeMay et al. |
| 8,556,845 B2 | 10/2013 | LeMay et al. |
| 8,571,883 B2 | 10/2013 | Dougherty, Jr. et al. |
| 8,585,668 B2 | 11/2013 | Pauley et al. |
| 8,696,957 B2 | 4/2014 | Dougherty, Jr. et al. |
| 8,735,647 B2 | 5/2014 | Schoelling |
| 8,961,449 B2 | 2/2015 | Jorgensen et al. |
| 9,107,775 B2 | 8/2015 | Edgett et al. |
| 9,125,771 B2 | 9/2015 | Schoelling |
| 9,173,778 B2 | 11/2015 | Schoelling |
| 9,192,522 B2 | 11/2015 | Edgett et al. |
| 2002/0120243 A1 | 8/2002 | Kraemer et al. |
| 2002/0156442 A1 | 10/2002 | Jackson et al. |
| 2003/0131456 A1 | 7/2003 | Rajala et al. |
| 2003/0149416 A1 | 8/2003 | Cole et al. |
| 2003/0158533 A1 | 8/2003 | Agyapong et al. |
| 2003/0208180 A1 | 11/2003 | Fuchs et al. |
| 2003/0225389 A1 | 12/2003 | Cassoni et al. |
| 2004/0019317 A1 | 1/2004 | Takagi et al. |
| 2004/0126555 A1 | 7/2004 | Hartmann et al. |
| 2004/0193131 A1 | 9/2004 | Wada |
| 2005/0059944 A1 | 3/2005 | Jackson et al. |
| 2005/0096619 A1 | 5/2005 | Costa |
| 2007/0026228 A1 | 2/2007 | Hartmann et al. |
| 2007/0234532 A1* | 10/2007 | Gilbert ............. A61F 13/2051 28/118 |
| 2007/0260211 A1 | 11/2007 | Schmidt-Forst |
| 2008/0065041 A1 | 3/2008 | Stan et al. |
| 2008/0097366 A1 | 4/2008 | Matthews |
| 2008/0110005 A1 | 5/2008 | Gilbert et al. |
| 2008/0119811 A1 | 5/2008 | Gilbert et al. |
| 2008/0221502 A1 | 9/2008 | Binner et al. |
| 2008/0262464 A1 | 10/2008 | Hasse et al. |
| 2008/0287902 A1 | 11/2008 | Edgett et al. |
| 2009/0036859 A1 | 2/2009 | Dougherty, Jr. et al. |
| 2009/0082712 A1 | 3/2009 | Hasse et al. |
| 2009/0156979 A1 | 6/2009 | Andersch |
| 2009/0227975 A1 | 9/2009 | Dougherty, Jr. et al. |
| 2009/0234268 A1 | 9/2009 | Jorgensen et al. |
| 2009/0247981 A1 | 10/2009 | Glaug et al. |
| 2009/0281474 A1 | 11/2009 | Dougherty, Jr. et al. |
| 2009/0281514 A1 | 11/2009 | Dougherty, Jr. et al. |
| 2010/0036309 A1 | 2/2010 | Jorgensen, Jr. et al. |
| 2010/0056981 A1 | 3/2010 | Karapasha et al. |
| 2010/0120707 A1 | 5/2010 | Dougherty, Jr. et al. |
| 2010/0198133 A1 | 8/2010 | Dougherty, Jr. et al. |
| 2011/0224637 A1 | 9/2011 | Edgett et al. |
| 2012/0061867 A1 | 3/2012 | Dougherty, Jr. et al. |
| 2013/0018347 A1 | 1/2013 | Edgett et al. |
| 2014/0265026 A1 | 9/2014 | Schoelling |
| 2014/0276523 A1 | 9/2014 | Schoelling |
| 2015/0105711 A1 | 4/2015 | LeMay et al. |
| 2015/0320608 A1 | 11/2015 | Edgett et al. |

FOREIGN PATENT DOCUMENTS

| | | |
|---|---|---|
| CA | 2441647 A1 | 5/1996 |
| CA | 2180789 A1 | 1/1997 |
| CA | 2312666 A1 | 1/2001 |
| CA | 108982 A1 | 8/2006 |
| CA | 115880 A1 | 8/2008 |
| FR | 2207687 | 6/1974 |
| FR | 2505176 A | 11/1982 |
| GB | 1108197 A | 4/1968 |
| GB | 2073592 | 10/1981 |
| GB | 9306074 A | 5/1993 |
| IE | 8904080 A | 6/1990 |
| IL | 109027 | 6/1994 |
| JP | SHO44004240 | 2/1944 |
| JP | 62-8754 | 1/1987 |
| JP | 63-212358 | 9/1988 |
| JP | H05-68695 | 3/1993 |
| JP | 2001-008964 | 1/2001 |
| JP | 2005-526584 | 9/2005 |
| JP | SHO62-027952 | 9/2005 |
| WO | WO9933428 A1 | 7/1999 |
| WO | WO0006071 A1 | 2/2000 |
| WO | WO0124729 A1 | 4/2001 |
| WO | WO0166055 A1 | 9/2001 |
| WO | WO02058587 A1 | 8/2002 |
| WO | WO03101362 A2 | 11/2003 |
| WO | WO2005041883 A1 | 5/2005 |
| WO | WO2005112856 A1 | 12/2005 |
| WO | WO2005112862 A1 | 12/2005 |
| WO | WO2006016933 A1 | 2/2006 |
| WO | WO2007078413 A1 | 2/2007 |
| WO | WO2008056339 A1 | 5/2008 |
| WO | WO200809331 A1 | 8/2008 |
| WO | WO2008144624 A1 | 11/2008 |
| ZA | 8803191 | 11/1988 |
| ZA | 9706745 | 2/1998 |

OTHER PUBLICATIONS

English Translation of Decision of Rejection against Japanese Patent Application No. 2012-506079; Date Mailed Jan. 7, 2013; pp. 1-4.

International Search Report for PCT/US2010/030351 dated Jun. 3, 2010.

PCT International Search Report, International Application No. PCT/US2008/064074, International Filing Date May 19, 2008, Mailing Date Jul. 21, 2008.

First Office Action Against JP Application No. 2010-508629, Dated Dec. 20, 2011.

International Search Report dated Jun. 2, 2008, for International application No. PCT/*S07/13749.

Written Opinion dated Jun. 2, 2008, for International application No. PCT/US07/13749.

English Translation of Decision of Rejection against Japanese Patent Application No. 2010-508629; Date Mailed Dec. 27, 2012; pp. 1-3.

\* cited by examiner

TAMPON PLEDGET WITH IMPROVED BY-PASS LEAKAGE PROTECTION

This application is a divisional application of copending U.S. patent application Ser. No. 12/115,845, filed May 6, 2008, now abandoned, the contents of which being incorporated by reference herein in its entirety.

TECHNICAL FIELD

This invention is directed to tampons and, more particularly, to tampons having improved absorbency characteristics and anti-leak abilities.

BACKGROUND OF THE INVENTION

Tampon leakage typically ranges from about 15% to about 20% incidence of tampon leakage for all sizes of tampons. Most leakage is attributed to the bypass of blood or other body fluids from the vagina during menstruation, such bypass being due to a less-than-optimal fit of the tampon within the vagina. The propensity of any commercially-produced tampon to leak is highly unpredictable due to tampons being mass produced and further due to wide anatomical variations among users. Both MRI (magnetic resonance imaging) analysis with actual users as well as ION simulations (anthropometrically correct simulation devices) indicate that a higher likelihood of bypass leakage exists when the tampon is inserted high into the vaginal canal and angled to either the right or left side of the fornices of the vagina.

Figure 1A:
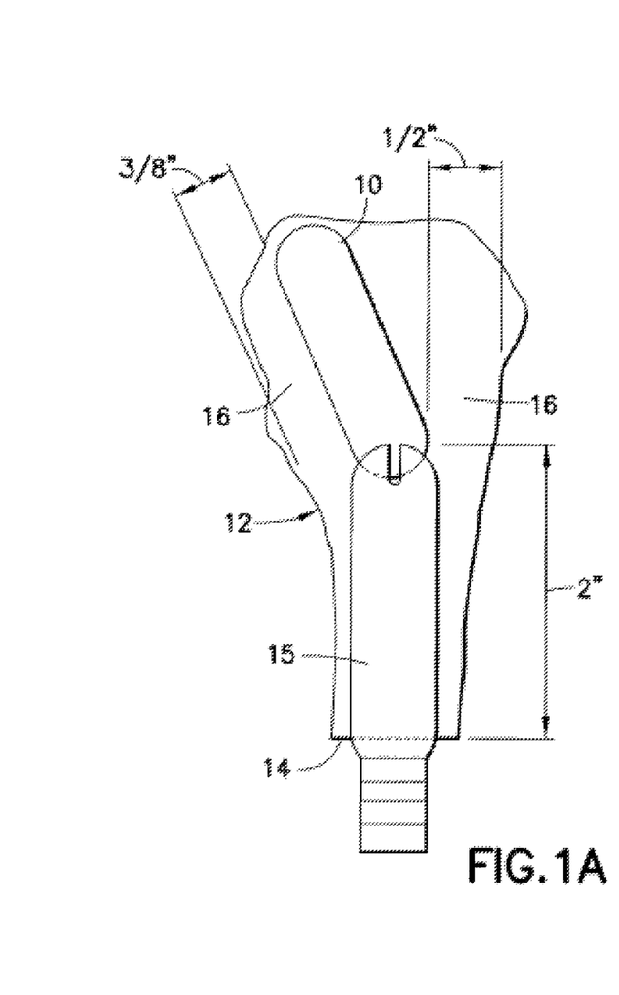
FIG. 1A is a side view of a Regular tampon of the related art in a dry state inserted high into a vagina and angled to one side of the fornices.
Figure 1B:
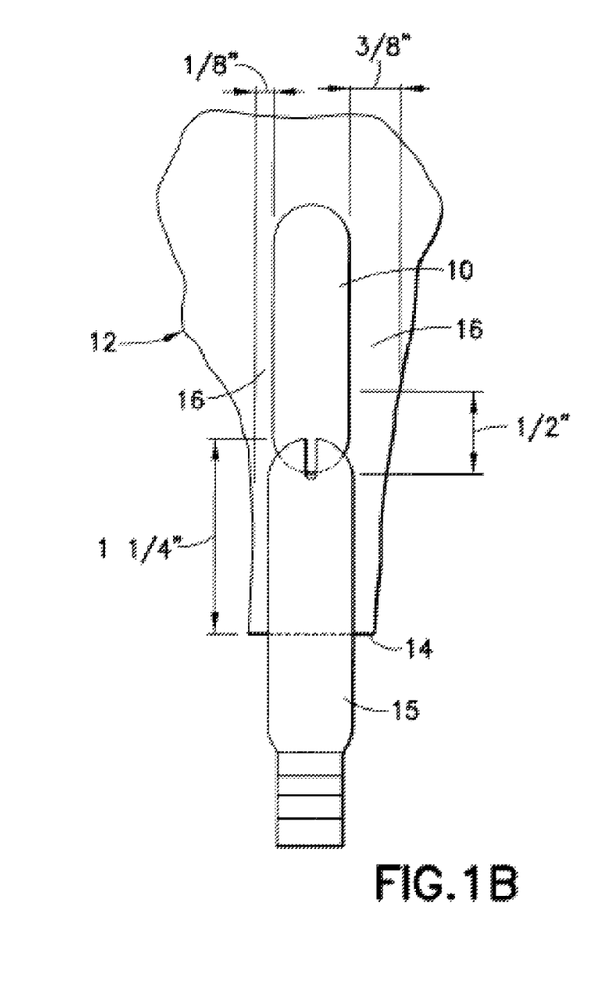
FIG. 1B is a side view of a Regular tampon of the related art in a dry state inserted low into a vagina.

As is shown in FIGS. 1A and 1B, the approximate location of a typical tampon 10 inserted into a vagina 12 through a tampon applicator 15 is shown. The tampon 10 is a Regular absorbency tampon as defined by the FDA. As used herein, the term "Regular" with regard to tampons means a tampon having a dry width of about 0.48 inches. In FIG. 1A, the tampon 10 is inserted into the vagina using an applicator into a "high" position, which means the tampon is inserted farther than is required to provide for the suitable absorption of body fluids. As shown, the tampon 10 is in a dry state (i.e., before the absorption of a significant amount of body fluid). When inserted to this position, which is about 2 inches beyond the introitus 14, the tampon 10 is angled to one side of the fornices (not shown) such that gaps 16 are defined between the sides and edges of the tampon and at least some of the wall of the vagina 12. These gaps 16 undesirably allow for the flow of body fluids past the tampon 10.

In FIG. 1B, the tampon 10 is again illustrated in the dry state and is inserted into the vagina 12 into a "low" position using the applicator (shown at 15). In the low position, the tampon is inserted to just inside the introitus 14 about 1.25 inches. When inserted to this position, gaps 16 are defined between the sides and edges of the tampon 10 and the wall of the vagina 12. The gaps 16 undesirably allow for the flow of body fluids past the tampon 10.

Figure 2A:
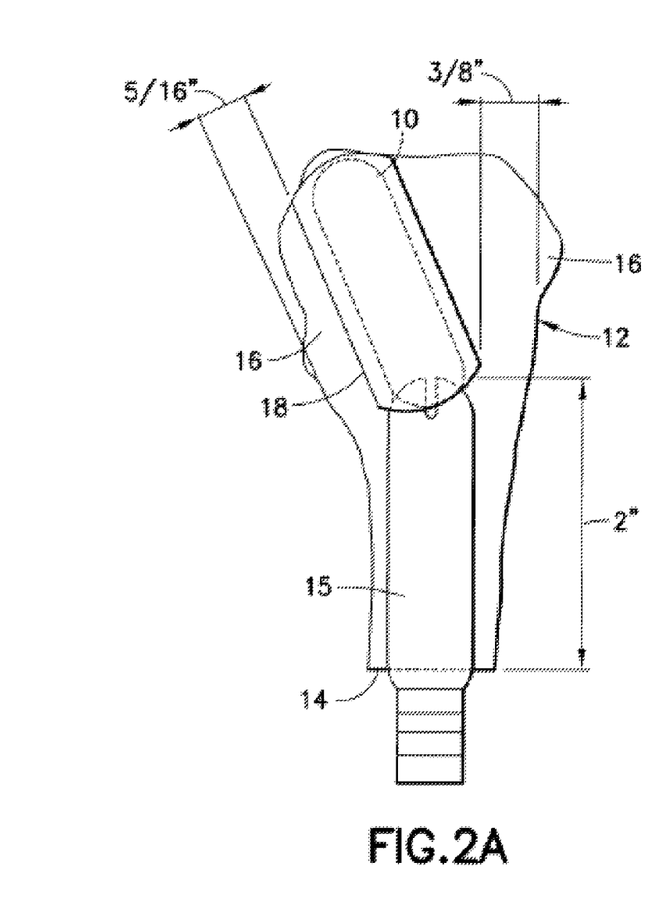
FIG. 2A is a side view of a Regular tampon of the related art in an expanded state inserted high into a vagina and angled to one side of the fornices.
Figure 2B:
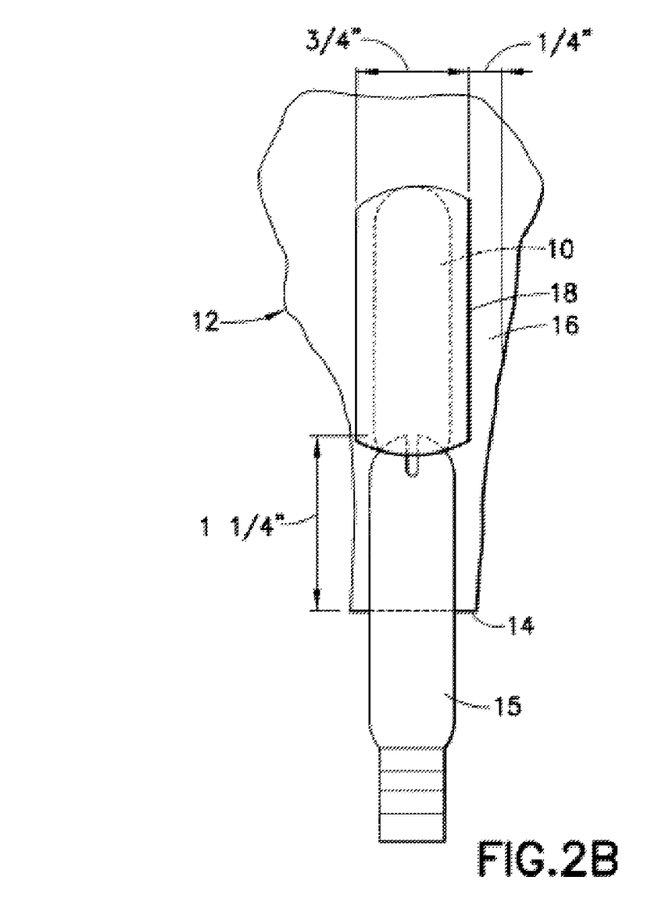
FIG. 2B is a side view of a Regular tampon of the related art in an expanded state inserted low into a vagina.

In FIGS. 2A and 2B, the approximate location of the Regular tampon 10 inserted into the vagina 12 through a tampon applicator 15 into the high position is again shown. In FIG. 2A, the tampon 10 is in an expanded state (i.e., after the absorption of a significant amount of body fluid). When inserted to this position (again about 2 inches beyond the introitus 14), the tampon 10 is again angled to one side of the fornices. However, even in the absorbed state in which the material of the tampon 10 blooms or expands upon contact with body fluids, gaps 16 are still defined between sides 18 of the tampon 10 and the wall of the vagina 12 and undesirably allow for the flow of body fluids past the tampon.

In FIG. 2B, the tampon 10 is again illustrated in the expanded state, but it is inserted into the vagina 12 into the low position. Even with blooming of the tampon 10, the sides 18 of the tampon do not close off the gaps 16 defined between the tampon and the wall of the vagina 12.

Figure 3A:
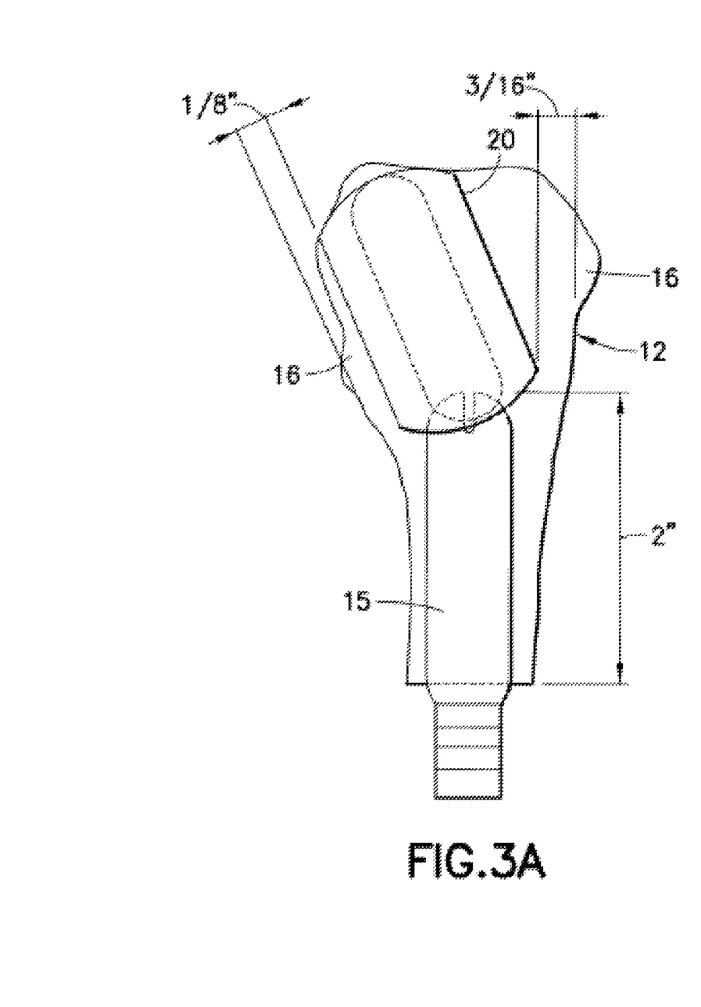
FIG. 3A is a side view of a Super tampon of the related art in an expanded state inserted high into a vagina and angled to one side of the fornices.
Figure 3B:
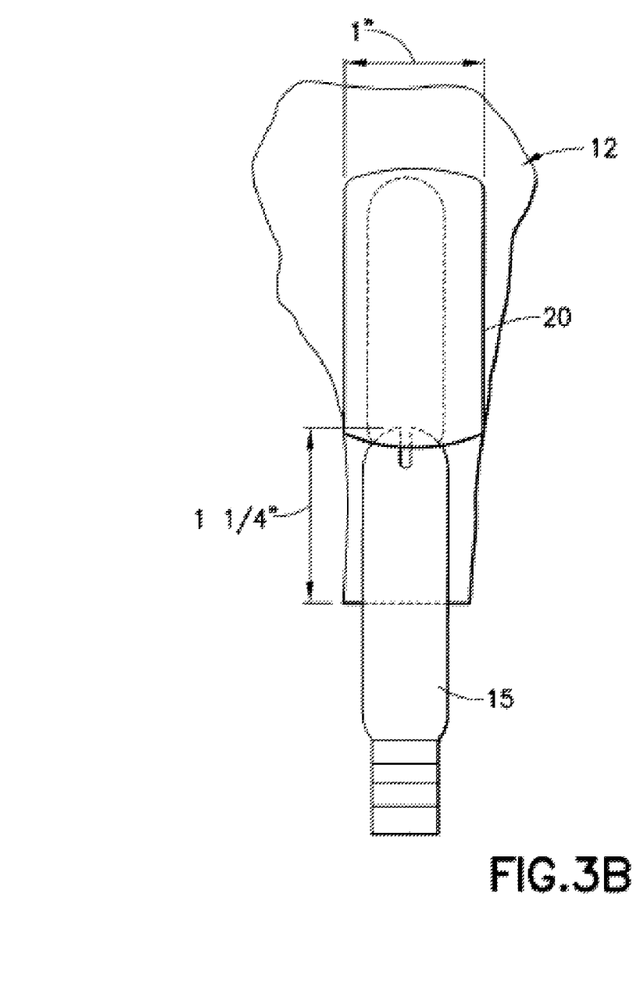
FIG. 3B is a side view of a Super tampon of the related art in an expanded state inserted low into a vagina.

As is shown in FIGS. 3A and 3B, the approximate location of a typical Super absorbency (as defined by FDA regulations) tampon 20 inserted into the vagina 12 through a tampon applicator 15 is shown. The tampon 20 is shown in the expanded state. As used herein, the term "Super" with regard to tampons means a tampon having a dry width of about 0.54 inches. In FIG. 3A, the tampon 20 is inserted high into the vagina 12 and is angled to one side of the fornices. Even though the tampon 20 is of the Super configuration, gaps 16 are defined between the bloomed outer surfaces of the tampon and the wall of the vagina 12. In FIG. 3B, when the tampon 20 is inserted into the vagina 12 in the low position, the gaps are eliminated or at least significantly reduced, particularly after blooming. However, movement on the part of the user may cause the tampon 20 to shift in the vagina 12, thereby causing the outer surfaces of the tampon to be spaced from the wall of the vagina, thereby further allowing leakage to occur around the tampon. Larger sizes of the tampon (e.g., "Super Plus" absorbency) may alleviate some of the problem; however, it is still possible and likely that gaps would be formed.

Given the above-described problems with tampons, it is contemplated that users would prefer tampon products with improved absorption capabilities to avoid by-pass leakage. Also, if additional protection features were incorporated into the tampon design, users would feel that they have a "second line of defense" against leakages, thereby giving them more control over their period. The present invention meets these needs.

SUMMARY OF THE INVENTION

In one aspect, the present invention resides in a tampon having two pledgets and a leak shield located therebetween. The pledgets and the leak shield are folded such that the leak shield covers most of the surface of at least one of the pledgets. Both pledgets have absorbencies that are each greater than an absorbency of the leak shield.

In another aspect, the present invention resides in a tampon having a pledget having a first absorbency and a leak shield covering at least a portion of the pledget and having a second absorbency. The second absorbency (of the leak shield) is less than the first absorbency (of the pledget). The leak shield comprises a polymer film that is impervious to fluid.

In another aspect, the present invention resides in a tampon having a pledget with a first absorbency, a leak shield positioned adjacent the pledget and covering at least a portion thereof, and a hydrophilic absorbent layer positioned adjacent the leak shield. The leak shield is a blend of polymer film and non-woven resilient material and is hydrophobic and impervious to fluid, particularly body fluids. The hydrophilic nature of the absorbent layer, in combination with the hydrophobic nature of the leak shield, causes fluid to be transferred from the leak shield to the absorbent layer.

In another aspect, the present invention resides in a method of fabricating a tampon. In this method a first pledget is formed. A fluid-impervious polymer material is also combined with an absorbent material to define a polymer laminate. The polymer laminate is then registered on an opening of an oven tube such that the absorbent material is in contact with the opening of the oven tube. The first pledget and the polymer laminate are then rammed into the oven tube. The polymer laminate is then stitched to the first pledget using a string.

One advantage of the present invention is that in the dual pledget configuration (due to the lower pledget), the tampon has superior absorbency characteristics. These absorbency characteristics are improved over the absorbency characteristics of conventional tampons. Considering that gravity has a considerable effect on the flow of menstrual fluids when the user is standing or engaged in activity, the presence of the lower pledget provides "backup" protection against leakage. Thus, even in instances in which the tampon has a less-than-optimal fit in the vagina (due to, for example, anatomical variations among users, activity, or the like), the user can rest assured that she will have sufficient protection against the loss of body fluid around the tampon.

Another advantage of the present invention is that the material of the leak shield assists in preventing the user's fingers from becoming soiled during tampon removal. When the material of the pledget absorbs body fluids, the leak shield operates to contain those body fluids. Even though a string is typically used to pull the tampon from the vagina, the user often grasps tampon with her fingers and applies pressure. In doing so, the material of the leak shield (such as the fluid-impervious material) acts as a bag and maintains the body fluid in the tampon as opposed to allowing the body fluid to be squeezed out of the pledget material and onto the user's fingers.

Yet another advantage of the present invention is the fact that the opening edges of the anti-leak shield are facing upwards against the flow of the menstrual fluid, allowing it to be more capable to contain the fluid flowing downwards (like a cup). In addition, the upper edges of the anti-leak shield are "free" to open up, away from the pledget itself (in the manner of an umbrella), and catch by-pass menstrual fluid, thus reducing the possibility of leakage.

DETAILED DESCRIPTION OF THE INVENTION

A tampon that mitigates and/or alleviates by-pass leakage is provided by the present invention. In Table 1, information indicative of the amount of expansion necessary to reduce tampon by-pass leakage is presented.

TABLE 1

| | | Tampon dimensions | | | | | | | | | | |
|---|---|---|---|---|---|---|---|---|---|---|---|---|
| | | High injection | | Low injection | | | | | High injection | | Low injection | |
| Tampon | Dry width | Left gap | Right gap | Left gap | Right gap | Wet width | of wet vs. dry width | % diff. wet/dry | Left gap | Right gap | Left gap | Right gap |
| Regular | 0.48 | 0.38 | 0.5 | 0.13 | 038 | 0.71 | 0.23 | 48 | 0.31 | 0.38 | 0 | 0.25 |
| Super | 0.54 | 0.35 | 0.47 | 0.1 | 035 | 0.98 | 0.44 | 81 | 0.13 | 0.19 | 0 | 0 |

In comparing the regular and super size tampons to generate the above data, dimensions of a vagina were taken from an ION Simulator. These dimensions represented one person's anthropometric measurements. The gap dimensions were taken from a one-dimensional configuration with respect to the vagina. The tampons tested were taken from one dated lot number of product.

Based on the above data, positioning the tampon lower in the vagina reduced the size of the gaps from which bypass leakage emanated. For placement of the tampon higher in the vagina, it was determined that a bloom to approximately 1.5 inches was needed to suitably plug the gaps. For placement of the tampon lower in the vagina, it was determined that a bloom to approximately 1.1 inches was needed to suitably plug the gaps. Thus, for the regular size tampon, a bloom of about 213% was needed, and for the super size tampon, a bloom of about 178% was needed.

In order to provide the user with adequate protection against bypass leakage, particularly in instances in which greater than 200% bloom is desired, a dual pledget design with leak shields incorporated therein was developed to arrive at the tampons of the present invention.

Figure 4:
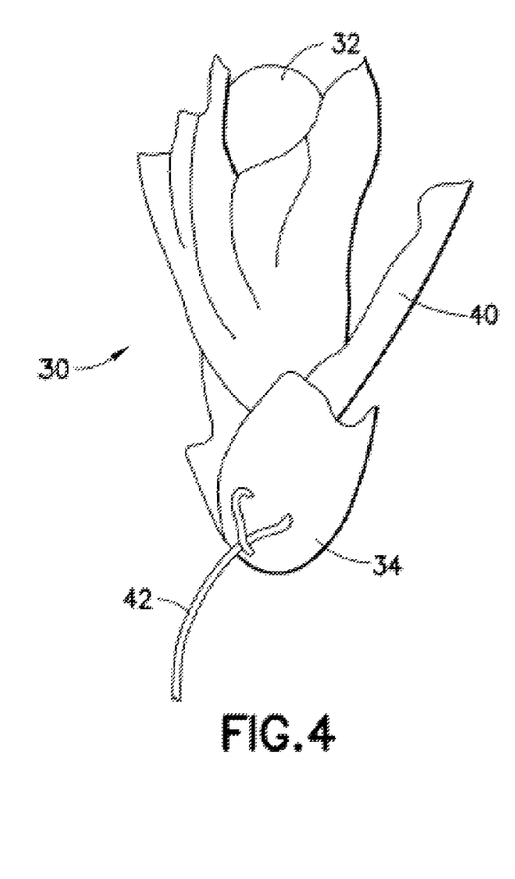
FIG. 4 is a side view of one embodiment of a tampon of the present invention.

As is shown in FIG. 4, a tampon having dual pledgets and a leak shield is generally designated by the reference numeral 30 and is hereinafter referred to as "tampon 30." The tampon 30 includes an upper pledget 32, a lower pledget 34, a leak shield 40 located between the upper and lower pledgets, and a string 42 secured to at least the lower pledget. Both the upper pledget 32 and the lower pledget 34 have greater abilities to absorb fluid than the leak shield 40. In use, the leak shield 40 receives and absorbs fluid that bypasses the upper pledget 32. Such fluid is generally received from lateral directions and is wicked to both the upper pledget 32 and the lower pledget 34 where the fluid is further absorbed. The leak shield 40 also functions as a sheath for the upper pledget 32 and covers a majority thereof, thereby providing comfort during the removal of the tampon 10. The string 42, in addition to stitching the upper pledget 32, the lower pledget 34, and the leak shield 40 together, facilitates the removal of the tampon 30 from the vagina.

Figure 5:
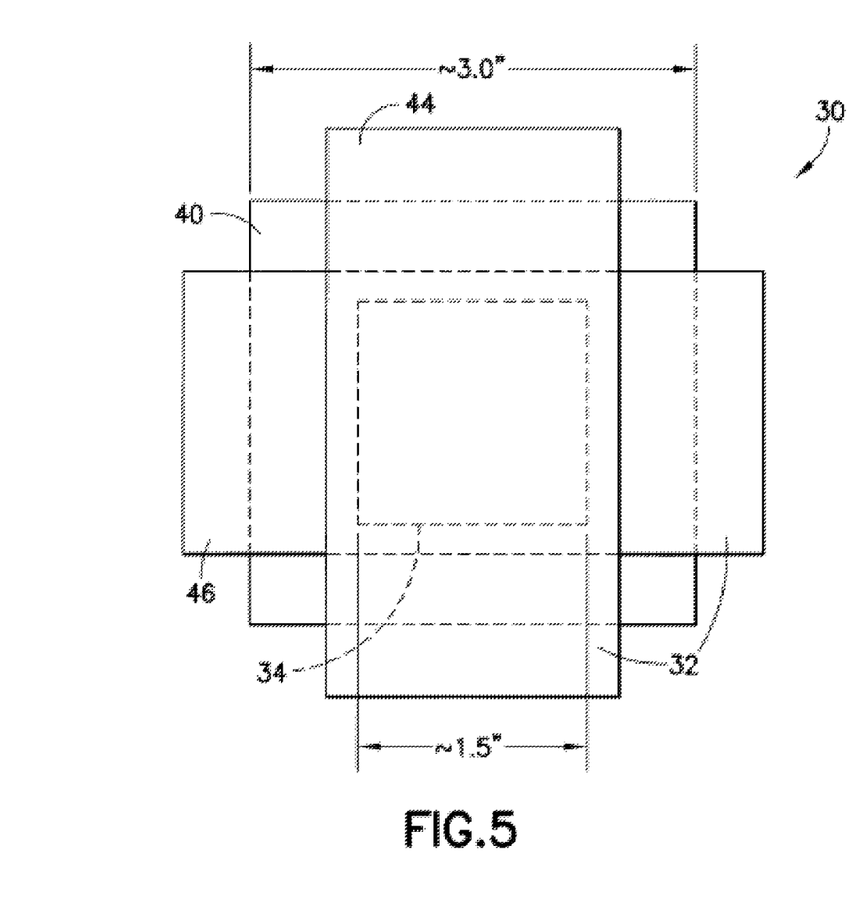
FIG. 5 is a schematic view of the materials of the tampon of FIG. 4.

As is shown in FIG. 5, in one embodiment, the upper pledget 32 comprises an inner layer 44 and an outer layer 46 arranged together. The materials of the inner layer 44, the outer layer 46, the leak shield 40, and the lower pledget 34 are each cut or otherwise formed to be angular in shape to maximize cost savings and to promote efficiency in the process of manufacturing the tampon 30. In the manufacture of a Regular tampon, the leak shield 40 is about 3 inches by about 3 inches square, and the lower pledget 34 is about 1.5 inches by about 1.5 inches square. The present invention is not limited in these regards, however, as one or both the leak shield 40 and the lower pledget 34 may be defined by other geometrical shapes (e.g., round), and the leak shield and the lower pledget may be of other dimensions. Furthermore, the present invention is not limited to one layer of material for the leak shield 40, as multiple layers of material may be used. Additionally, more material can be used to produce a Super tampon, and less material can be used to produce a Light absorbency tampon. In this embodiment, the dimensions of the leak shield 40 may range from 1.0 inches to 4.0 inches in square or rectangular form. A single or dual layer is preferred, but it may also comprise of several layers of material, especially when using nanofibers.

The leak shield 40 is formed of an absorbent material. One example of absorbent material that could be used for the leak shield 40 is a carded, thermal bonded, non-woven material (e.g., stock number SH-PPC-33 from Shalag Industries LTD., located in Upper Galilee, Israel, which has a basis weight of 33 gsm (grams per square meter) (30% cotton/70% polypropylene)). One example of an absorbent material that could be used for the lower pledget 34 is a hydro-entangled composite material (e.g., stock number KK-072 from Polymer Group, Inc., Mooresville, N.C., which has a basis weight of 4.0 osy (ounces per square yard) (50% rayon/50% PET (polyethylene terephthalate)).

Figure 6:
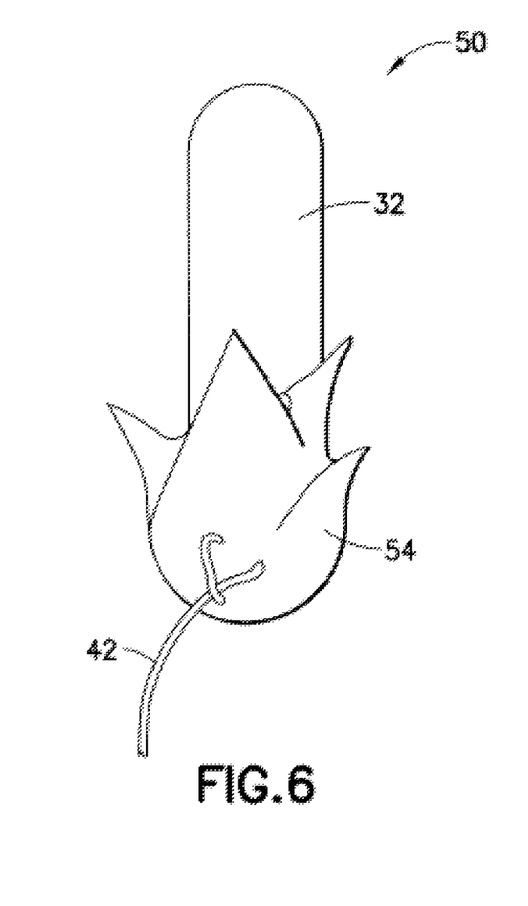
FIG. 6 is a side view of another embodiment of a tampon of the present invention having a leak shield.

As is shown in FIG. 6, another embodiment of a tampon is designated by the reference numeral 50. The tampon 50 includes the upper pledget 32 comprising the inner layer 44 and the outer layer 46 as well as a leak shield that is a fluid-impervious layer, which is designated by the reference numeral 54. The fluid-impervious layer 54 comprises a polymer film or two or more materials to form a polymer laminate. In some embodiments, the polymer film(s) may be micro-porous, thereby resulting in a breathable device. Given the nature of the polymer material used to make the film, the smooth surface of the film allows the fluid-impervious layer 54 to more effectively disengage from the upper pledget 32 and open upon insertion into the vagina. When the pledgets and the fluid-impervious layer 54 are folded together into the tampon form, the fluid-impervious layer functions as a collector of body fluids and allows the tampon to have an extended service life before finally leaking at full saturation. The string 42 is attached to the fluid-impervious layer 54.

Figure 7:
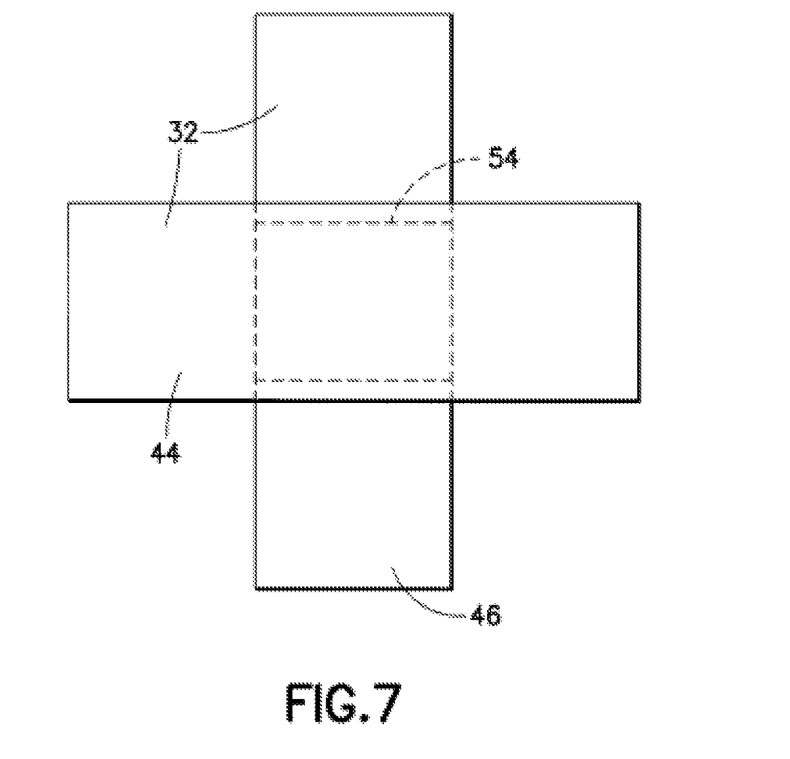
FIG. 7 is a schematic view of the materials of the tampon of FIG. 6.
Figure 8:
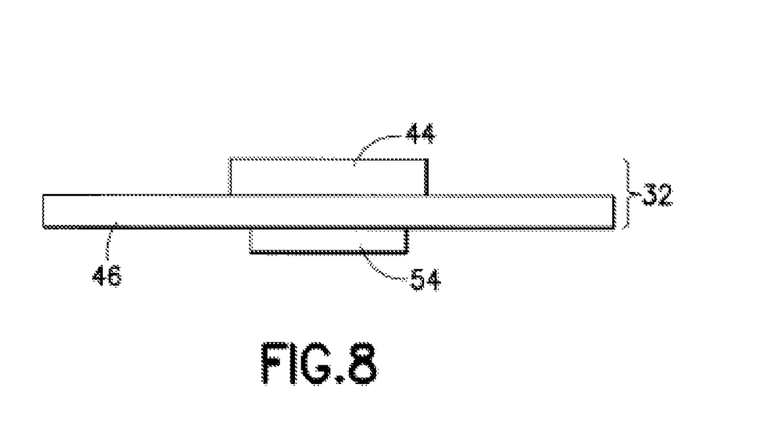
FIG. 8 is a schematic view of the materials of the tampon of FIG. 6.

As is shown in FIGS. 7 and 8, prior to forming the tampon, the fluid-impervious layer 54 is located under the bottom surface of the outer layer 46 of the upper pledget 32. The outer layer 46 is positioned under the inner layer 44. When the tampon is folded, the fluid-impervious layer 54 provides the function of the leak shield as previously described.

In still another embodiment of the present invention, the leak shield may additionally or alternatively be a fluid-repellent or hydrophobic layer. In this embodiment, the hydrophobic layer may be a material that is one or more of non-woven, laminated, meltblown, micro-porous, and apertured polymer material. In one embodiment applying the hydrophobic layer "post" pledget forming, one exemplary non-woven material is an SMS (spunbond/meltblown/spunbond) material in which the meltblown layer is thicker than either of the two adjacent spunbond layers and has fluid-repelling properties, thereby resulting in high hydro-head values. As used herein, the term "hydro-head" refers to a measure of the liquid barrier properties of a layer of fabric, and a test utilizing hydro-head values determines the height of water which the layer of fabric will support before a predetermined amount of liquid passes therethrough. Non-woven materials with nanofibers or small denier fibers that are uniformly distributed throughout the material are also within the scope of the present invention. SMS non-woven material is available from Avgol Nonwoven Industries in Holon, Israel, in basis weights of 10 to 36 gsm.

In another embodiment applying the hydrophobic layer "pre" pledget forming, one exemplary non-woven material is a carded thermal bonded web comprising of 100% polyester fibers (e.g., polyethylene terephthalate (PET)). This material would be available in 17 gsm basis weight (code SH-PT-17) from Shalag Industries LTD. in Upper Galilee, Israel.

One exemplary manner of applying either the fluid-impervious layer 54 or the hydrophobic layer to the bottom surface of the outer layer 46 is to dip the bottom portion of the upper pledget 32 into a bath of liquefied polymer material (such as polyurethane or the like) that is curable into a solid. Once dipped, the upper pledget 32 can be removed and dried with air, heat, or light to effect the curing of the polymer material into the fluid-impervious layer 54 or the hydrophobic layer.

Although a hydrophobic non-woven is fluid repellent by itself, it is hydrophilic when in intimate contact with an absorbent member, such as the pledget. This would be the preferred execution for anti-leak shields. It would absorb fluid while in contact with the pledget. Once it breaks free from the pledget after saturation, it would act like a "raincoat" shield that would capture the menstrual fluid and direct it back to the pledget, due to gravity and the upward configuration of the anti-leak shield's open edges.

The present invention may also incorporate hydrophilic non-woven material comprising SBPP (spunbond polypropylene) containing a surfactant finish.

Figure 9:
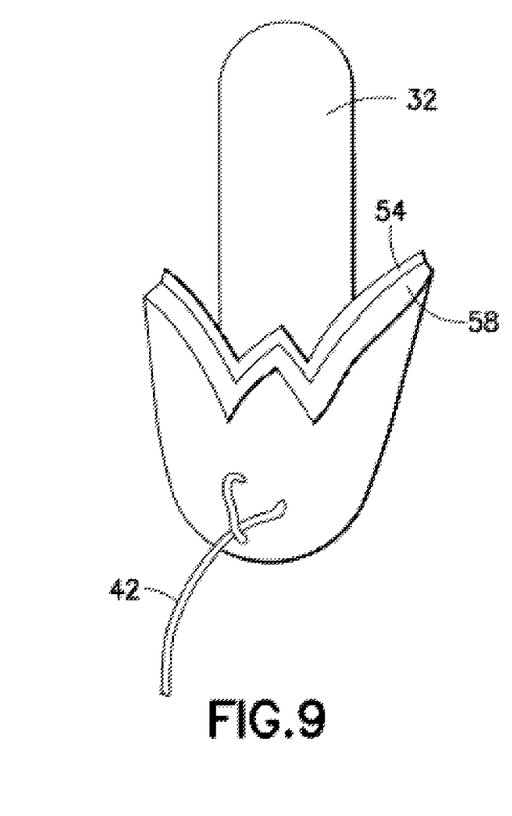
FIG. 9 is a side view of another embodiment of a tampon of the present invention having a hybrid layer.
Figure 10:
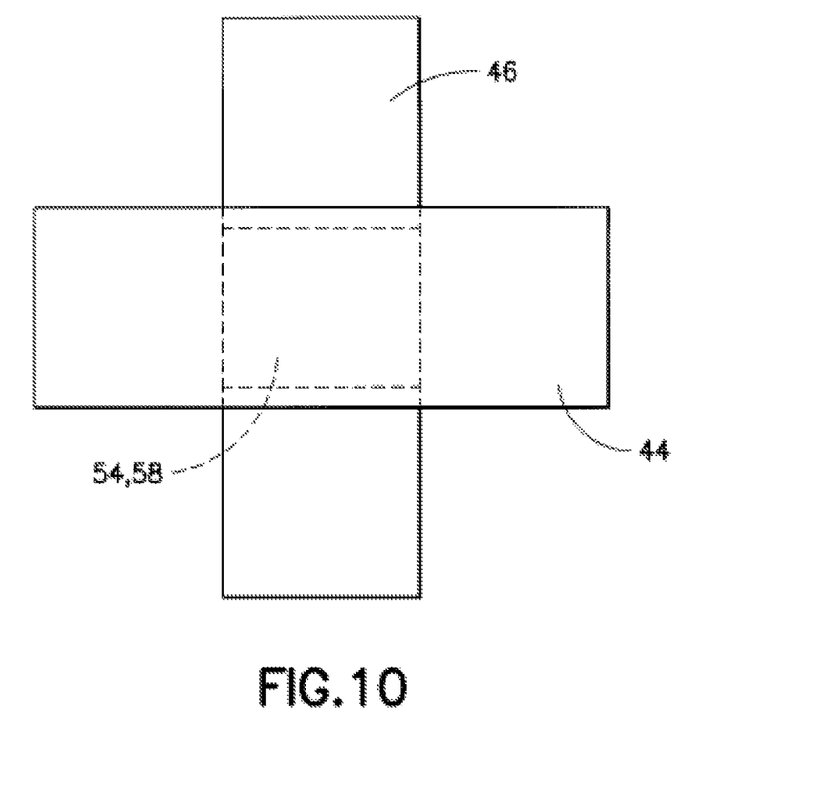
FIG. 10 is a schematic view of the materials of the tampon of FIG. 9.
Figure 11:
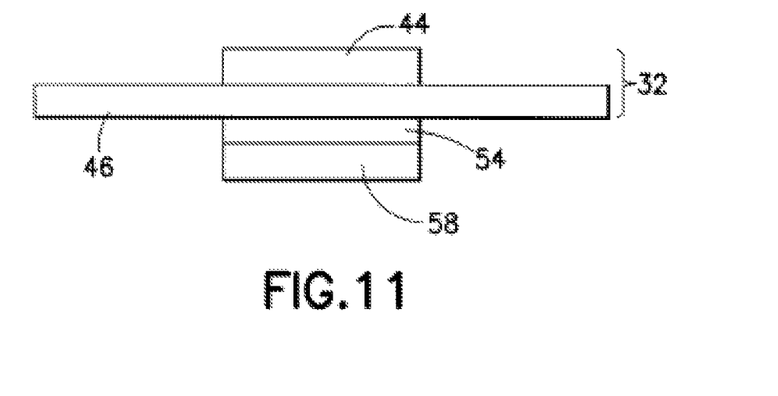
FIG. 11 is a schematic view of the materials of the tampon of FIG. 9.

As is shown in FIG. 9, the fluid-impervious layer 54 may be a "hybrid," which as used herein means a blend of polymer film and non-woven resilient material. The upper pledget 32 and the string 42 are the same as or similar to those previously described. As is shown in FIGS. 9-11, the fluid-impervious layer 54 is located under the bottom surface of the outer layer 46 of the upper pledget 32. The inner layer 44 is positioned over the outer layer 46. An absorbent layer 58 may be disposed under the fluid-impervious layer 54. This absorbent layer 58, which is hydrophilic and functions as a "second line of defense" against leakage that may get around the fluid-impervious layer 54, may be non-woven, airlaid, spunlaced, hydro-entangled, tissue, flocked, or the like. The present invention is not limited in this regard as other forms of the absorbent layer 58 may be utilized. The absorbent layer 58 is flexible and soft, thereby providing comfort to the user during use and during removal of the tampon.

Figure 12:
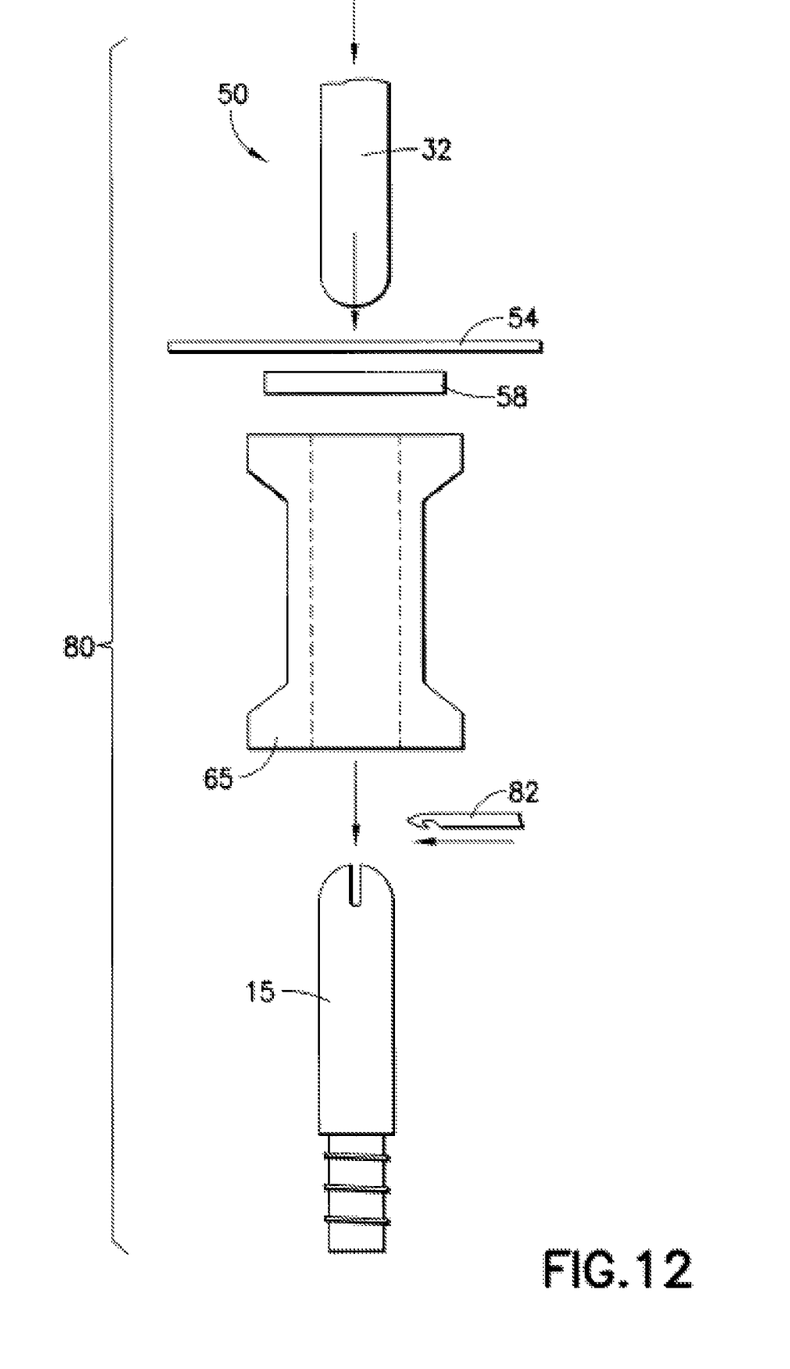
FIG. 12 is an exploded schematic view of a process of assembling one tampon of the present invention.

Referring now to FIG. 12, one process of manufacturing the tampon 50 of the present invention is designated generally by the reference numeral 80. In the process 80, the fluid-impervious layer 54 and the absorbent layer 58 are pre-combined and arranged into a web to form the polymer laminate. The polymer laminate is then attached to the upper pledget 32 after the upper pledget has been formed and set using heat. In doing so, the polymer laminate is unwound from the web of material, cut to a specified size, placed on a vacuum roll, and then transferred and registered on top of a transfer tube 65. The absorbent side of the polymer laminate is in contact with the transfer tube 65. The upper pledget 32 (along with the polymer laminate defined by the fluid-impervious layer 54 and the absorbent layer 58) is then rammed into the transfer tube 65 and pushed to the bottom of the tube. Using a needle 82, the string 42 is then used to stitch the fluid-impervious layer 54 and the absorbent layer 58 to the bottom of the upper pledget 32 such that the absorbent layer is located at the bottom (string side) of the tampon. The tampon 50 is then inserted into the barrel of an applicator 15.

When both a fluid-impervious layer 54 and the absorbent layer 58 are incorporated into the design of a tampon, the material of the fluid-impervious layer and the material of the absorbent layer are bonded, laminated, heat-sealed, or otherwise adhered to each other to be in interfacial engagement in line on the machine used to form the tampons. In embodiments in which the fluid-impervious layer 54 and the absorbent layer 58 are ultrasonically bonded together, the material of the absorbent layer preferably includes polymeric fibers that are compatible with the polymeric material of the fluid-impervious layer.

The present invention is not limited with regard to the above process, as other processes may be used to form the tampons of the present invention. For example, the upper pledget 32 can be formed and can be thermally set in an oven tube prior to attaching the leak shield via transfer tube. In this embodiment, the upper pledget 32 may be set in an oven tube having a diameter that is smaller than the diameter of the oven tube used for the upper pledget 32 only. This will create a smaller diameter pledget and thus enable additional materials (such as the leak shield 40 and the lower pledget 34) to be accommodated in the tampon applicator without increasing the ejection force.

The lower pledget 34 can be formed from a web of suitable material by being unwound from the web, cut to a specified size, spaced to a specified gap (spacing between material pieces with respect to a continuous web), passed onto a vacuum transfer drum, and aligned and registered on top of a non-woven web of the leak shield 40. The lower pledget 34 is then ultrasonically bonded or heat sealed to the non-woven web.

The non-woven web can be cut in the middle of the gaps and registered and centered on top of a transfer tube. The upper pledget 32, which has been pre-fabricated, can then be inserted into the transfer tube such that the lower pledget 34 and the leak shield 40 are pushed down into the transfer tube along with it. The transfer tube is optionally subjected to no or very low temperature heat. Finally, the assembled tampon (the upper pledget 32, the lower pledget 34, and the leak shield 40) are ejected from the transfer tube and stitched together with the string 42.

Figure 13:
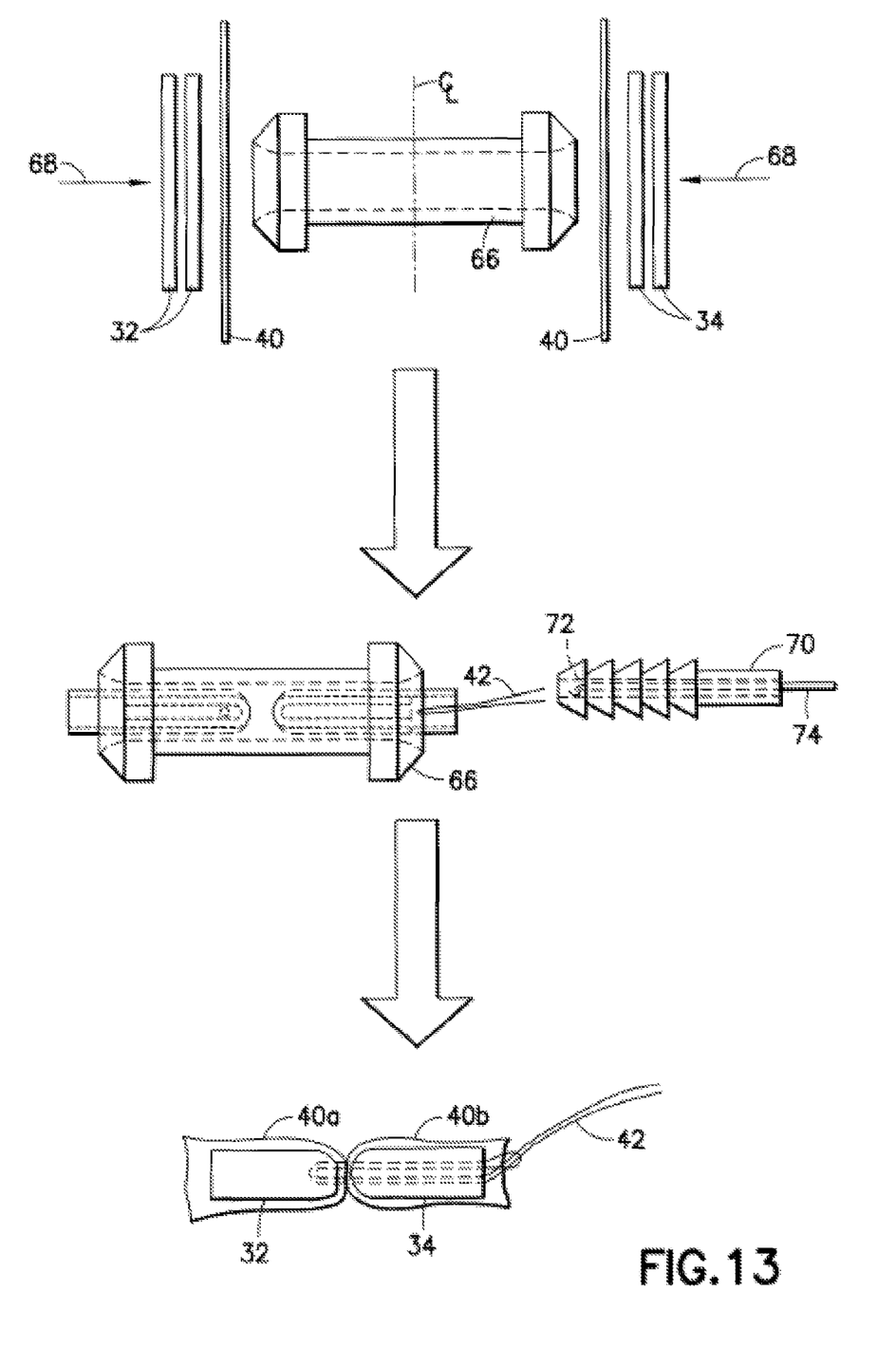
FIG. 13 is an exploded schematic view of another process of assembling a tampon of the present invention.

As is shown in FIG. 13, another process of manufacturing a tampon of the present invention is shown. In this process, an oven tube 66 having dual openings (one at each end) receives material for the upper pledget 32 in one opening and material for the lower pledget 34 in the opposite opening. One or both openings also receive leak shield material 40. The pledget materials and the leak shield material 40 are inserted into the oven tube 66 in the directions of arrows 68 using rams 70. One of the rams 70 includes a longitudinal bore 72 located therein in which a needle 74 can be accommodated to stitch the string 42 into the finished tampon. The finished tampon includes an upper leak shield 40a that covers the upper pledget 32 and a lower leak shield 40b that covers the lower pledget 34.

Figure 14A:
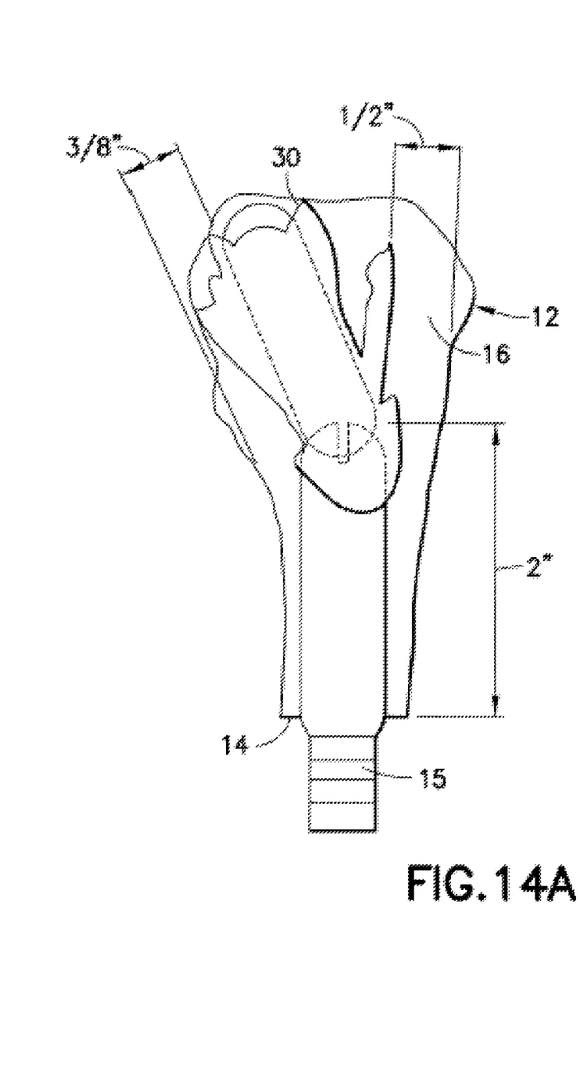
FIG. 14A is a side view of a Regular tampon of the present invention in a dry state inserted high into a vagina and angled to one side of the fornices.
Figure 14B:
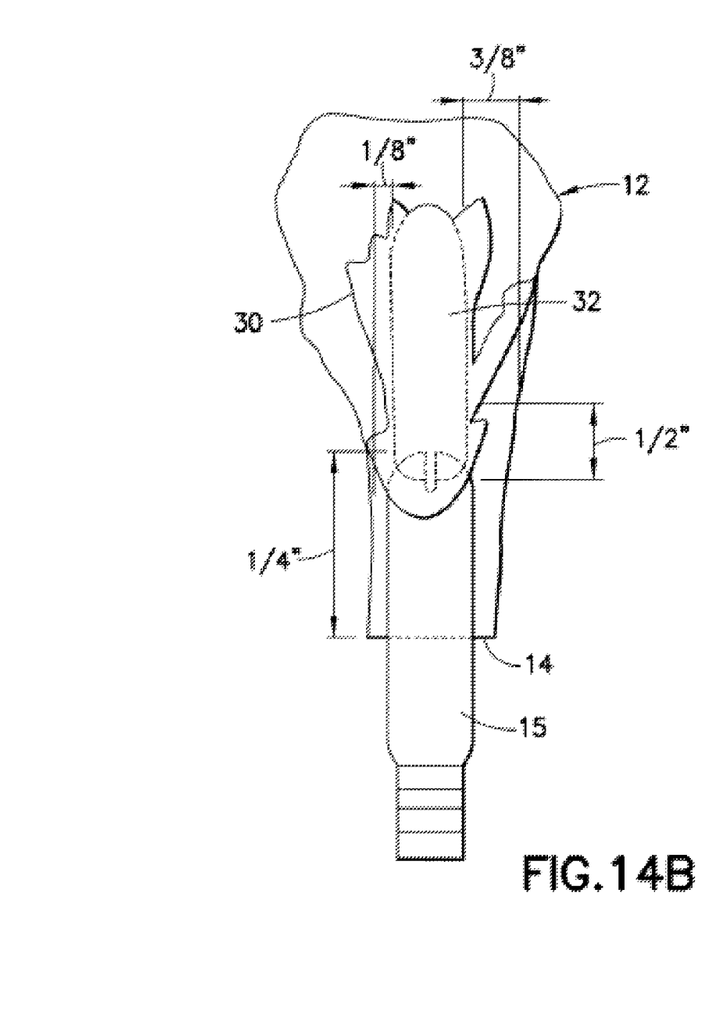
FIG. 14B is a side view of a Regular tampon of the present invention in a dry state inserted low into a vagina.

Referring now to FIGS. 14A and 14B, the approximate location of a Regular tampon 30 of the present invention in the vagina 12 is shown. Although tampon 30 is depicted, the present invention is not limited in this regard as other tampons of the present invention (for example, tampon 50 or any other tampon of the present invention having a fluid-impervious or hydrophobic layer) can be depicted. In these Figures, the tampon 30 is illustrated in the dry state. In FIG. 14A, the tampon 30 is inserted into the high position in the vagina 12, i.e., about 2 inches beyond the introitus 14 where it is angled to one side by the fornices. A gap 16 may be defined between the outer surfaces of the tampon 30 and the walls of the vagina 12.

As is shown in FIG. 14B, the tampon 30 is inserted into the low position in the vagina 12, i.e., about 1.25 inches beyond the introitus 14 using the applicator 15. When inserted into the low position, the gaps between the outer surfaces of the tampon 30 and the walls of the vagina 12 are eliminated due to the expansion (blooming) of the upper pledget 32.

Figure 15A:
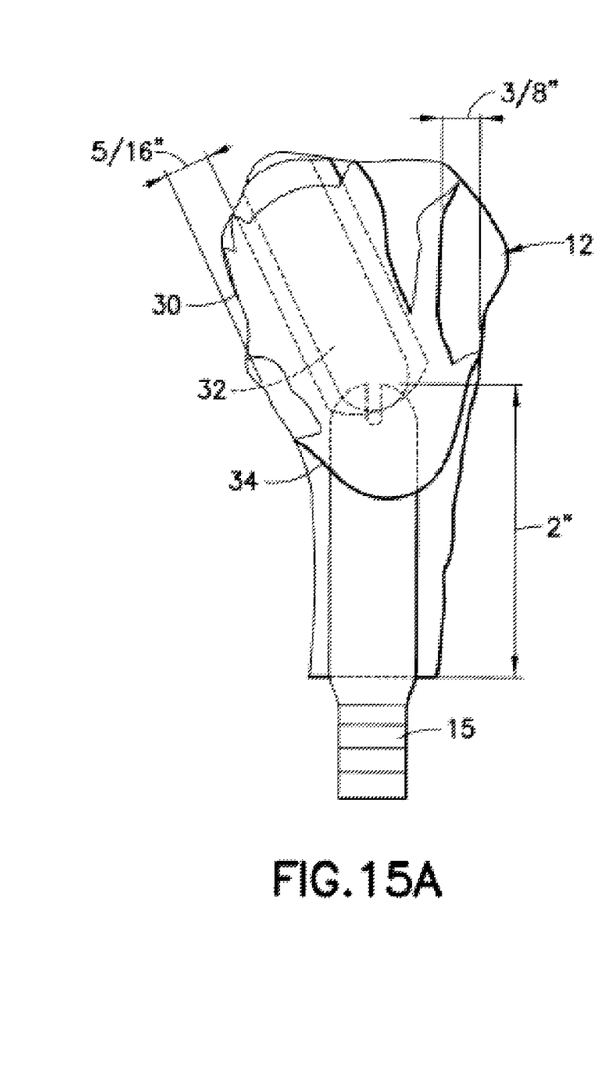
FIG. 15A is a side view of a Regular tampon of the present invention in an expanded state inserted high into a vagina and angled to one side of the fornices.
Figure 15B:
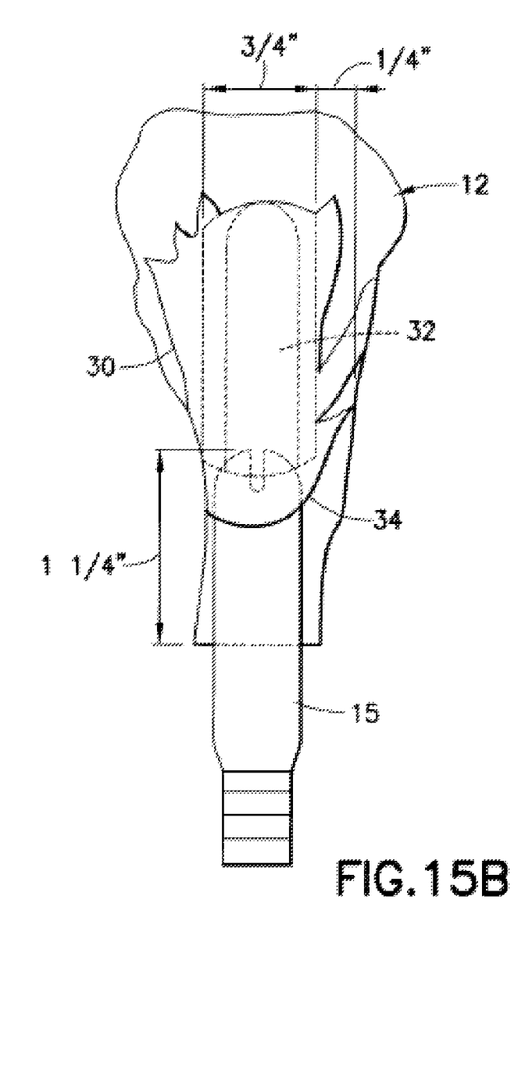
FIG. 15B is a side view of a Regular tampon of the present invention in an expanded state inserted low into a vagina.

Referring now to FIG. 15A and 15B, the approximate location of the Regular tampon 30 in the expanded state in the vagina 12 is shown. In FIG. 15A, the tampon 30 is in the high position in the vagina 12. Due to the absorption of body fluids by the dual pledget configuration of tampon 30 and the blooming of the lower pledget 34, gaps between the outer surfaces of the tampon and the walls of the vagina 12 are eliminated. In FIG. 15B, a similar configuration is realized even though the tampon 30 is inserted into the low position in the vagina 12 using the applicator 15. In the low position, the blooming of both the upper pledget 32 and the lower pledget 34 eliminate the gaps between the tampon 30 and the vagina wall.

Although this invention has been shown and described with respect to the detailed embodiments thereof, it will be understood by those of skill in the art that various changes may be made and equivalents may be substituted for elements thereof without departing from the scope of the invention. In addition, modifications may be made to adapt a particular situation or material to the teachings of the invention without departing from the essential scope thereof. Therefore, it is intended that the invention not be limited to the particular embodiments disclosed in the above detailed description, but that the invention will include all embodiments falling within the scope of the appended claims.

The invention claimed is:

1. A method of fabricating a tampon, comprising the steps of:
    forming an absorbent first pledget;
    combining a fluid-impervious polymer material with an absorbent material to define a polymer laminate;
    registering said polymer laminate on an opening of an oven tube such that said absorbent material is in contact with said opening of said oven tube;
    ramming said absorbent material first pledget and said polymer laminate into said oven tube; and
    stitching said polymer laminate to said first pledget using a string.

2. The method of claim 1, further comprising the step of inserting said fabricated tampon into an applicator barrel.

3. The method of claim 1, wherein said fluid-impervious polymer material is ultrasonically bonded to an absorbent material.

4. The method of claim 1, wherein said absorbent first pledget is formed by combining two or more layers of said fluid impervious polymer material with said absorbent material to define said polymer material.

5. The method of claim 1, wherein said absorbent first pledget is formed by combining said fluid-impervious polymer material with at least two layers of said absorbent material to define said polymer laminate.

6. The method of claim 5, wherein said second layer of said at least two layers of said absorbent material has a greater absorbency than said first layer of said absorbent material.

7. The method of claim 5, wherein said step of forming said absorbent first pledget further comprises the steps of:
    forming said absorbent first pledget to have a top portion and a bottom portion;
    dipping said bottom portion into a bath of liquefied polymer material;
    removing said bottom portion from said bath of liquefied polymer material; and
    curing said liquefied polymer material on said bottom portion into a solid.

8. The method of claim 7, wherein said step of curing said liquefied polymer material on said bottom portion into a solid is done by one or more of air, heat or light.

9. The method of claim 1, further comprising the step of forming one of an absorbent second pledget or absorbent layer, wherein said polymer laminate on said first pledget is between said absorbent first pledget and one of said absorbent second pledget or absorbent layer.

10. The method of claim 9, wherein one of said absorbent second pledget and absorbent layer are formed such that one of said absorbent second pledget and said absorbent layer has an absorbency that is greater than said absorbency of said polymer laminate.

11. The method of claim 9, wherein one of said absorbent second pledget and said absorbent layer is bonded, laminated, heat-sealed, or otherwise adhered to said polymer laminate.

12. The method of claim 11, wherein one of said absorbent second pledget and said absorbent layer and said polymer laminate are in interfacial engagement in line during formation.

13. The method of claim 9, wherein one of said absorbent second pledget and said absorbent layer are ultrasonically bonded to said polymer laminate.

14. A method of fabricating a tampon, comprising the steps of:
    forming an absorbent first pledget;
    combining a first fluid-impervious polymer material with a first absorbent material to define a first polymer laminate;
    registering said first polymer laminate on a first opening of an oven tube such that said first absorbent material is in contact with said first opening of said oven tube;
    ramming said absorbent first pledget and said first polymer laminate through said first opening of said oven tube;
    forming an absorbent second pledget;
    combining a second fluid-impervious polymer material with a second absorbent material to define a second polymer laminate;
    registering said second polymer laminate on a second opening of said oven tube such that said second absorbent material is in contact with said second opening of said oven tube;
    ramming said absorbent second pledget and said absorbent layer through said second opening of said oven tube; and
    stitching said first polymer laminate and said second polymer laminate together with a string.

15. The method of claim 14, wherein at least one of said first polymer laminate and said second polymer laminate are formed by ultrasonic bonding.

16. The method of claim 14, wherein a ram used during ramming either said absorbent first pledget or said absorbent second pledget has a length and a width, wherein said ram has a bore running along said length of said ram, wherein a needle is accommodated within said bore such that said needle stitches said first polymer laminate and said second polymer laminate together with a string.

17. The method of claim 14, further comprising the step of inserting said fabricated tampon into an applicator barrel.

18. The method of claim 14, wherein said step of forming one or more of said absorbent first pledget and said absorbent second pledget further comprises the steps of:
    forming one or more of said absorbent second pledget to have a top portion and a bottom portion;
    dipping said bottom portion into a bath of liquefied polymer material;
    removing said bottom portion from said bath of liquefied polymer material; and
    curing said liquefied polymer material on said bottom portion into a solid.

19. A method of assembling a tampon, comprising the steps of:
    forming an absorbent first pledget;
    inserting said absorbent first pledget with a first ram into a first end of an oven tube, said first ram having a longitudinal bore;
    inserting a needle into said longitudinal bore;
    stitching a string onto said absorbent first pledget with said needle through said longitudinal bore;
    ejecting said absorbent first pledget from said oven tube; and inserting said absorbent first pledget into an applicator barrel.

20. The method of assembling a tampon of claim 19, wherein said absorbent first pledget comprises an outer layer and an inner layer, and wherein forming said absorbent first pledget includes an additional step of placing said outer layer adjacent said inner layer and folding said outer layer and said inner layer to form a generally cylindrical shape.

21. The method of assembling a tampon of claim 20, wherein forming said absorbent first pledget includes said additional step of placing said outer layer adjacent said inner layer such that said outer layer is positioned under said inner layer.

22. The method of assembling a tampon of claim 20, wherein said step of ejecting said absorbent first pledget from said oven tube provides said absorbent first pledget having a width of about 0.54 inches.

23. The method of assembling a tampon of claim 20, wherein said step of ejecting said absorbent first pledget from said oven tube provides said absorbent first pledget having a width of about 0.48 inches.

24. The method of assembling a tampon of claim 19, further comprising the step of inserting said absorbent first pledget into an applicator barrel.

* * * * *